(12) United States Patent
Tsutsui et al.

(10) Patent No.: US 10,022,401 B2
(45) Date of Patent: Jul. 17, 2018

(54) PHARMACEUTICAL CONTAINING DENDRITIC CELLS, AND METHOD FOR PRODUCING SAME

(71) Applicant: National University Corporation Hokkaido University, Sapporo-shi (JP)

(72) Inventors: Hiroyuki Tsutsui, Sapporo (JP);
Shintaro Kinugawa, Sapporo (JP);
Naoki Ishimori, Sapporo (JP);
Akimichi Saito, Sapporo (JP)

(73) Assignee: National University Corporation Hokkaido University, Hokkaido (JP)

(*) Notice: Subject to any disclaimer, the term of this patent is extended or adjusted under 35 U.S.C. 154(b) by 0 days.

(21) Appl. No.: 15/121,557

(22) PCT Filed: Feb. 26, 2015

(86) PCT No.: PCT/JP2015/055547
§ 371 (c)(1),
(2) Date: Aug. 25, 2016

(87) PCT Pub. No.: WO2015/129791
PCT Pub. Date: Sep. 3, 2015

(65) Prior Publication Data
US 2016/0361358 A1    Dec. 15, 2016

(30) Foreign Application Priority Data
Feb. 26, 2014  (JP) .................. 2014-036070

(51) Int. Cl.
*A01N 63/00* (2006.01)
*A01N 65/00* (2009.01)
*A61K 35/15* (2015.01)
*C12N 5/0784* (2010.01)

(52) U.S. Cl.
CPC ............ *A61K 35/15* (2013.01); *C12N 5/0639* (2013.01); *C12N 2500/34* (2013.01); *C12N 2500/36* (2013.01); *C12N 2501/22* (2013.01); *C12N 2501/2302* (2013.01)

(58) Field of Classification Search
None
See application file for complete search history.

(56) References Cited

U.S. PATENT DOCUMENTS 6,531,453 B1 * 3/2003 Taniguchi .......... A61K 31/7032
424/579
2003/0153073 A1 * 8/2003 Rogers ................ C12N 5/0636
435/372

2006/0148723 A1  7/2006 Yamamura et al.
2010/0008954 A1  1/2010 Wong et al.
2010/0129339 A1  5/2010 Taniguchi et al.

FOREIGN PATENT DOCUMENTS

| CN | 102978160 A | 3/2013 |
| WO | WO 03/016326 A1 | 2/2003 |
| WO | WO 2007/043630 A1 | 4/2007 |
| WO | WO 2012/018950 A1 | 2/2012 |

OTHER PUBLICATIONS

Ayach et al., PNAS, 103(7):2304-309 (2006).*
Knorr et al., Frontiers Physiol., 5(295):1-7 (2014).*
Nahrendorf et al., JEM, 204(12):3037-3047 (2007).*
Nahrendorf et al., Circ., 121:2437-2445 (2010).*
Cheng et al, J. Clin. Immunol., 25(3):246-253 (2005).*
Naito et al., J Immunol., 181:5691-5701 (2008).*
Kinugawa et al., J. Clin. Exp. Med., 246(3) :229-234 (2013).*
Tsutsui et al., Junkan Plus, 15(3):2-6 (2015).*
Cao et al., Am. J. Physiol. Gastrointest. Liver Physiol., 297:G249-58 (2009).
Godfrey and Berzins, Nat. Rev. Immunol., 7:505-18 (2007).
Homma et al., J. Mol. Cell. Cardiol., 62:179-88 (2013).
PCT/JP2015/055547 International Search Report issued by Japanese Patent Office dated May 26, 2015.
Ishikawa et al., Int. J. Cancer, 117:265-73 (2005).
Ishikawa et al., Clin. Cancer Res., 11:1910-17 (2005).
Miellot et al., Eur. J. Immunol, 35:3704-13 (2005).
Molling et al., J. Immunol. Methods, 322:70-81 (2007).
Pal et al., J. Immunol., 166:662-68 (2001).
Ronet et al., J. Immunol, 175:899-908 (2005).
Saito A. et al., "Activation of invariant natural killer T cells ameliorates the development of angiotensin II-mediated abdominal aortic aneurysm formation in obese ob/ ob mice.", Nov. 19, 2013, American Heart Association Scientific Session 2013, [searched on Feb. 25, 2014], internet http://www.abstractsonline.com/plan/ViewAbstract.aspx?mID=3281&sKey=b063f1cf-d113-4296-bdf4-48183826fa33&cKey=02cc3289-0d67-466d-bd4b-c9473388e726&mKey=951e351e-429c-4b2e-84d0-8da73bOOde45#.

(Continued)

*Primary Examiner* — Thomas J. Visone
(74) *Attorney, Agent, or Firm* — RatnerPrestia (57) ABSTRACT

[Problem] The purpose of the present invention is to provide a novel pharmaceutical for use in cellular immunotherapy for the prevention and/or treatment of diseases in which Th2-type cytokines are effective, such as cardiovascular disease and the like.
[Solution] The present invention relates to a pharmaceutical containing dendritic cells pulsed with α-galactosylceramide for the prevention and/or treatment of diseases in which Th2-type cytokines are effective, and a method for producing the same.

1 Claim, 3 Drawing Sheets

(56) References Cited

OTHER PUBLICATIONS

Saito et al., Activation of Invariant Natural Killer T Cells Ameliorates the Development of Angiotensin II-Mediated Abdominal Aortic Aneurysm Formation in Obese ob/ob Mice, Circulation, vol. 128, A11427, entire text (2013).
Sharif et al., Nat. Med, 7(9):1057-62 (2001).
Singh et al., J. Exp. Med, 194(12):1801-11 (2001).
Sobirin et al., Circ. Res., 111:1037-47 (2012).
Tashiro, Biosci. Biotechnol. Biochem., 76(6):1055-67 (2012).
Van Kaer, Nat. Rev. Immunol., 5:31-42 (2005).
Motohashi et al., J. Immunol, 182:2492-501 (2009).
Cheng et al., J. Cardiac Failure, 15(2):158-62 (2009).
Luc Van Kaer, Nature Reviews Immunology, 5:31-42 (2005).
Nakai et al., Blood, 104(7):2051-59 (2004).

* cited by examiner

PHARMACEUTICAL CONTAINING DENDRITIC CELLS, AND METHOD FOR PRODUCING SAME

CROSS-REFERENCE TO RELATED APPLICATIONS

This application is a U.S. National Phase Application of PCT International Application PCT/JP2015/055547, filed Feb. 26, 2015 which claims priority to Japanese Application No. 2014-036070, filed Feb. 26, 2014, the contents of which are incorporated herein by reference in their entireties for all purposes.

TECHNICAL FIELD

The present invention relates to a pharmaceutical containing dendritic cells pulsed with α-galactosylceramide for the prevention and/or treatment of diseases in which Th2-type cytokines are effective, and a method for producing the same.

BACKGROUND OF THE INVENTION

The cardiovascular diseases, such as myocardial infarction and cerebrovascular disorder, are the main cause of death, along with malignant tumors. Patients of heart failure which is the terminal state of these cardiovascular diseases, have substantially increased, and the number of such patients exceeds 1 million because of population aging, increased lifestyle-related disease causing heart failure, spread of acute stage therapy as well as improvement of treatment results in myocardial infarction, and the like.

By recent advances in drug therapy and non-drug therapy, prognosis of heart failure patients has been greatly improved. However, prognosis of severe cases is still poor even with these various therapies against heart failure, and patients in severe cases repeat hospitalizations due to its exacerbation, finally resulting in death. Therefore, there is a great need for development of a new therapeutic method for cardiovascular diseases, including myocardial infarction and heart failure.

Natural killer T (NKT) cells are a unique subset of T lymphocytes that simultaneously express NK cell markers and T cell receptors. Their T cell receptor has invariant α-chain, which is Vα14-Jα18 in mice and Vα24-Jα18 in humans. NKT cells are activated by recognizing glycolipid antigens presented by CD1d molecule that is an MHC class I-like molecule. The activated NKT cells rapidly produce large amounts of T helper (Th) type 1-cytokines of which representatives are interferon (IFN)-γ and tumor necrosis factor (TNF)-α, or Th2-type cytokines of which representatives are interleukins IL-4 and IL-10 in shaping subsequent adaptive immune response. Thus, NKT cells are believed to function as a bridge between the innate and adaptive immune system and to orchestrate tissue inflammation (Non-Patent Literature 1).

Although endogenous ligands of NKT cells have not become clear yet, α-galactosylceramide (α-GalCer) is known to specifically activate NKT cells (Non-Patent Literature 2), and many studies of NKT cells using α-GalCer have been reported. In the past animal experiments, it was reported that type 1 diabetes, autoimmune encephalomyelitis, rheumatoid arthritis, enteritis, and hepatic ischemia-reperfusion injury were improved by the administration of α-GalCer (Non-Patent Literatures 3 to 7). In addition, the present inventors have confirmed the therapeutic effects by systemic administration of α-GalCer in post-myocardial infarction heart failure models, cardiac ischemia-reperfusion injury models, and abdominal aortic aneurysm models (Non-Patent Literatures 8 to 10).

Such study results support the possibility that the activation of NKT cells by α-GalCer provides a new therapeutic method for cardiovascular diseases. However, clinical application of α-GalCer was difficult because the activation of NKT cells by α-GalCer was transient, the efficacy of α-GalCer was lowered when it was repeatedly administered, and the systemic administration of α-GalCer caused a liver damage.

In recent years, a technique of NKT cell activation by dendritic cells pulsed with α-GalCer has been developed (Non-Patent Literature 11), and clinical trials for lung cancer, and head and neck cancer were performed (Non-Patent Literature 12).

In cellular immunotherapy using NKT cells, control of the direction of the immune response of NKT cells affects the success of treatment. That is, when the diseases to be treated are those in which Th1-type cytokines are known to be therapeutically effective, such as cancers and infections, it is necessary to shift the immune response of NKT cells toward Th1 type. For example, in the clinical trials for lung cancer, and head and neck cancer mentioned above, a remarkable increase in the expression of IFN-γ, which is a Th1-type cytokine, is observed in the NKT cells used.

On the other hand, when the diseases to be treated are autoimmune disease, graft versus host disease and the like, it is necessary to shift the immune response of NKT cells toward Th2 type. For example, in an experimental autoimmune encephalomyelitis model, the condition was improved by the administration of antigen presenting cells treated with α-GalCer and anti-CD86 antibody to shift toward Th2 type (Non-Patent Literature 13).

Non-Patent Literature 13 has also revealed that the condition turns worse adversely by the administration of antigen presenting cells treated with α-GalCer and anti-CD40 antibody to shift toward Th1 type. This suggests that the control of immune responses of NKT cells is very important in the treatment of diseases and its improper control adversely exacerbates the disease.

For the treatment of cardiovascular diseases, it is important to induce NKT cells into the direction to produce Th2-type cytokines, mainly IL-10 (Non-Patent Literatures 8 to 10). Conventional methods for preparing α-GalCer-pulsed dendritic cells having an ability to shift the NKT cells toward Th2 type include, for example, a method of pulsing dendritic cells with an α-GalCer derivative as described in Patent Literature 1 in addition to the method using an anti-CD86 antibody described above, but such methods are not sufficient from the viewpoint of clinical applications, such as efficacy and safety.

CITATION LIST

Patent Literature

Patent Literature 1: WO2003/016326 pamphlet
Non Patent Literature
Non Patent Literature 1: Godfrey D I. et al., Nat. Rev. Immunol., 2007; 7: 505-518
Non Patent Literature 2: Van Kaer L. Nat. Rev. Immunol., 2005; 5: 31-42
Non Patent Literature 3: Cao Z. et al., Am. J. Physiol. Gastrointest. Liver Physiol., 2009; 297: G249-258

Non Patent Literature 4: Singh A K. et al., J. Exp. Med, 2001; 194:1801-1811

Non Patent Literature 5: Miellot A. et al., Eur. J. Immunol, 2005; 35: 3704-3713

Non Patent Literature 6: Ronet C. et al., J. Immunol, 2005; 175: 899-908

Non Patent Literature 7: Sharif S. et al., Nat. Med, 2001; 7: 1057-1062

Non Patent Literature 8: Sobirin M. A. et al., Circ. Res. 2012; 111: 1037-1047

Non Patent Literature 9: Homma T. et al., J. Mol. Cell. Cardiol. 2013; 62: 179-188

Non Patent Literature 10: Saito A. et al., "Activation of invariant natural killer T cells ameliorates the development of angiotensin II-mediated abdominal aortic aneurysm formation in obese ob/ob mice.", Nov. 19, 2013, American Heart Association Scientific Session 2013, [searched on Feb. 25, 2014], internet <http://www.abstractsonline.com/plan/ViewAbstract.aspx?mID=3281&sK ey=b063f1cf-d113-4296-bdf4-48183826fa33&cKey=02cc3289-0d67-466d-bd 4b-c9473388e726&mKey=951e351e-429c-4b2e-84d0-8da73b00de45#>

Non Patent Literature 11: Ishikawa E. et al., Int. J. Cancer 2005; 117: 265-273

Non Patent Literature 12: Ishikawa A. et al., Clin. Cancer Res. 2005; 11: 1910-1917

Non Patent Literature 13: Endre Pal. et al., J. Immunol. 2001; 166: 662-668

SUMMARY OF THE INVENTION

Technical Problems

An object of the present invention is to provide a novel pharmaceutical for use in cellular immunotherapy for the prevention and/or treatment of diseases in which Th2-type cytokines are effective, such as cardiovascular disease and the like.

Solution to Problem

As a result of intensive studies to solve the above problems, the present inventors have found, quite surprisingly, that administration of dendritic cells, prepared using a method known to prepare α-GalCer-pulsed dendritic cells having an ability to shift the immune response of NKT cells toward Th1 type, to an individual with cardiovascular disease in which Th2-type cytokines are supposed to be effective for the treatment, has led to improved survival rate and cardiac function. The following inventions have been completed based on these findings.

(1) A pharmaceutical for the prevention and/or treatment of cardiovascular disease, containing dendritic cells obtained by a method comprising the steps of:

culturing mononuclear cells in the presence of GM-CSF and IL-2, and pulsing the cultured cells with α-galactosylceramide.

(2) The pharmaceutical according to (1), wherein the cardiovascular disease is myocardial infarction or its complications, ischemia-reperfusion injury, or aneurysm.

(3) A method for producing a pharmaceutical for the prevention and/or treatment of cardiovascular disease, comprising the steps of:

culturing mononuclear cells in the presence of GM-CSF and IL-2, and pulsing the cultured cells with α-galactosylceramide.

Advantageous Effects of Invention

According to the present invention, it is possible to prevent and/or treat diseases in which Th2-type cytokines are effective, such as cardiovascular disease, using dendritic cells produced by a method conventionally known as a method for preparing dendritic cells having an ability to shift the immune response of NKT cells toward Th1 type. Since these dendritic cells can be prepared without requiring separation of a mononuclear cell fraction after culture and the cell preparation step can be simplified, there is an advantage in both operability and economic efficiency.

DETAILED DESCRIPTION OF THE INVENTION

A first aspect of the present invention relates to a pharmaceutical for the prevention and/or treatment of diseases in which Th2-type cytokines are effective, containing dendritic cells obtained by a method comprising the steps of culturing mononuclear cells in the presence of granulocyte-macrophage colony-stimulating factor (GM-CSF) and IL-2 and pulsing the cultured cells with α-GalCer. In addition, a second aspect of the present invention relates to a method for producing the pharmaceutical of the first aspect.

The dendritic cells contained in the pharmaceutical of the present invention are those obtained by a method comprising the steps of culturing mononuclear cells in the presence of GM-CSF and IL-2 and pulsing the cultured cells with α-GalCer.

The method for preparing dendritic cells contained in the pharmaceutical of the present invention comprises the steps of culturing mononuclear cells in the presence of GM-CSF and IL-2 (hereinafter referred to as culturing step) and pulsing the cultured cells with α-GalCer (hereinafter referred to as pulsing step). This method is described in, for example, Non-Patent Literature 11.

The culturing step is a step of culturing mononuclear cells isolated according to a conventional method, in a suitable medium containing GM-CSF and IL-2, by which the mononuclear cells are differentiation-induced into dendritic cells. The mononuclear cells can be isolated from a variety of animal tissues and can be typically separated by the method, such as density gradient centrifugation, for example, from peripheral blood or cell fraction collected by apheresis.

Considering safety upon subsequent administration of dendritic cells, mononuclear cells are preferably collected from an animal that is the same or closely related species of a subject to which dendritic cells derived therefrom are administered. For example, if the subject is a human, cells collected from a human of the same species are preferably used, and cells collected from a human itself receiving the administration, i.e. autologous mononuclear cells, are more preferably used.

The medium used in the culturing step and the pulsing step described later is a medium generally used when performing differentiation induction into dendritic cells from mononuclear cells, for example, such as AIM-V medium and RPMI-1640 medium, optionally supplemented with other components such as serum, plasma, or albumin. In the culturing step, the mononuclear cells are cultured for 5 to 10 days, using the medium supplemented with GM-CSF adjusted to a final concentration of 500 to 1000 U/mL, preferably about 800 U/mL, and IL-2 adjusted to a final concentration of 50 to 200 JRU/mL, preferably about 100 JRU/mL.

The pulsing step is a step of pulsing the dendritic cells prepared by the culturing step with α-GalCer, i.e. specifically, the dendritic cells are cultured in a medium containing α-GalCer having a final concentration of 50 to 200 ng/mL, preferably about 100 ng/mL, for 8 to 48 hours. The α-GalCer used in the pulsing step may include α-galactosylceramide itself, as well as salt, ester or derivative thereof (for example, those described in Tashiro T, Biosci. Biotechnol. Biochem. 2012; 76 (6): 1055-67). The α-GalCer can be purchased from Funakoshi Co., Ltd. and REGiMMUNE Co., Ltd.

The culturing step and the pulsing step may be carried out separately. The culturing step and the pulsing step may also be carried out at the same time by adding α-GalCer to the medium later in the culturing step.

The mononuclear cells and the dendritic cells obtained by the culturing step may be cryopreserved according to a conventional method and used in the subsequent step after being thawed when needed. Similarly, α-GalCer-pulsed dendritic cells obtained by the pulsing step can also be cryopreserved after preparation and used as a pharmaceutical of the present invention after being thawed when needed.

It is thought that the α-GalCer-pulsed dendritic cells prepared as described above induce or promote Th2-type cytokine production in the body of a subject having received the administration and thus exert a prophylactic and/or therapeutic effect on diseases. Such effects of the α-GalCer-pulsed dendritic cells can be confirmed by using an evaluation system that reflects the disease, for example, a disease model animal or a cell derived from the disease model animal. If the affection or onset of the disease is prevented by the dendritic cells, or if the condition of the disease is improved by the dendritic cells, or if the deterioration of the condition of the disease is suppressed, the dendritic cells are determined to have a preventive and/or therapeutic effect on the disease. The evaluation system as used herein is preferably an evaluation system for the diseases which is the same as or relevant to the disease that is scheduled for the treatment.

In one embodiment, the prophylactic and/or therapeutic effect of α-GalCer-pulsed dendritic cells can be confirmed by collecting a sample such as blood or the organ from a subject administered with α-GalCer-pulsed dendritic cells and measuring the amount of Th2-type cytokines or their gene expression level contained therein. The prophylactic and/or therapeutic effect of α-GalCer-pulsed dendritic cells can also be confirmed by collecting in advance a sample containing NKT cells from a subject, contacting the sample with α-GalCer-pulsed dendritic cells, and measuring the production amount of Th2-type cytokines or their gene expression level in the NKT cells.

Examples of Th2-type cytokines are IL-4, IL-10, IL-13, IL-21, TGF (Transforming growth factor)-β, and the like (Non-Patent Literature 1). When the amount of these cytokines or their gene expression level in the sample are increased by the α-GalCer-pulsed dendritic cells, such α-GalCer-pulsed dendritic cells are determined to be suitable for the prevention and/or treatment of diseases in which Th2-type cytokines are effective. Determination of the amount of these cytokines or their gene expression level can be carried out by an immunoassay, an RT-PCR method, or other methods known to a person skilled in the art.

The pharmaceutical according to the first aspect of the present invention can be used to prevent and/or treat diseases in which Th2-type cytokines are effective, by administration to a subject affected with such diseases or at risk of their affection.

The subject in the context of the present invention refers to any animal that may be affected with a disease in which Th2-type cytokines are effective, including preferably a mammalian individual, such as primates (e.g. human, chimpanzee, etc.), rodents (e.g. mouse, rat, guinea pig, hamster, etc.), Artiodactyla animals (e.g. cattle, goat, sheep, etc.), Perissodactyla animals (e.g. horse, etc.), and individuals of rabbit, dog, cat, etc., and more preferably a human individual, The disease in which Th2-type cytokines are effective (also referred to as "Th2-type cytokines remediable disease") means any disease that can be prevented and/or treated by administering a Th2-type cytokine to a subject, or by inducing or promoting the production of a Th2-type cytokine in the body of the subject, preferably any disease that can be prevented and/or treated by administering α-GalCer to a subject to induce or promote the production of a Th2-type cytokine in the body of the subject. These diseases include, for example, inflammatory diseases, autoimmune diseases or cardiovascular diseases, and among these diseases, cardiovascular diseases are especially suitable. The inflammatory disease includes graft versus host disease, hepatitis, cirrhosis, obstructive pulmonary disease, Crohn's disease, ulcerative colitis, Behcet's disease, and the like. The autoimmune disease includes rheumatoid arthritis, systemic lupus erythematosus, Sjogren's syndrome, polymyositis, dermatomyositis, scleroderma, hyperthyroidism, autoimmune adrenal gland dysfunction, pure red cell anemia, multiple sclerosis, rheumatoid carditis, and the like. In addition, the cardiovascular disease includes, for example, myocardial infarction; complications of myocardial infarction, such as heart failure, arrhythmia, papillary muscle rupture, myocardial rupture, ventricular aneurysm, and post-myocardial infarction syndrome; ischemia-reperfusion injury; or aneurysm.

In the treatment of a disease requiring a prompt treatment after the onset, such as myocardial infarction or the like, it is desirable to prepare in advance mononuclear cells, dendritic cells after the culturing step or α-GalCer-pulsed dendritic cells, cryopreserve such cells, prepare a pharmaceutical of the present invention quickly from the cryopreserved cells after the onset, and administer the pharmaceutical to patients in the acute phase.

The pharmaceutical of the present invention can be used for both purposes of the prevention and treatment of a disease. For the purpose of prevention, it is possible to prevent the affection or onset of a disease by administering the pharmaceutical of the present invention to a subject that may be affected with the disease. For example, it is possible to prevent the occurrence of myocardial infarction complications by administering the pharmaceutical of the present invention to a patient attacked by myocardial infarction. Also, in the case where treatment is intended, it is possible to slow the progress of a disease, stop the progress of a disease and improve the state of a disease, or cure a disease, by administering the pharmaceutical of the present invention to a subject suffering from the disease.

The pharmaceutical of the present invention comprises an effective amount of dendritic cells pulsed with α-GalCer. The "effective amount" as used herein means an amount effective to prevent and/or treat a disease. Such effective amounts may be appropriately adjusted by the type of diseases, the severity of symptoms, and the patients or other medical factors.

In a preferred embodiment of the pharmaceutical of the present invention, an effective amount of dendritic cells is $10^6$ to $10^9$ cells, preferably $10^7$ to $10^9$ cells, per body surface area of 1 m$^2$ of an individual to be administered.

The pharmaceutical of the present invention is usually used in the form of parenteral formulations such as injections, drip infusions, and the like. Carriers that can be used in the parenteral formulations include, for example, an aqueous carrier commonly used in cell formulations, such as saline and isotonic solutions comprising glucose, D-sorbitol, etc.

Furthermore, the pharmaceutical of the present invention may be a composition comprising pharmaceutically acceptable buffers, stabilizers, preservatives, and other components.

The pharmaceutically acceptable components are well known to a person skilled in the art, and the person skilled in the art can appropriately select and use the pharmaceutically acceptable components, for example from those described in Japanese Pharmacopoeia, sixteenth edition or other written standard, within the scope of his/her normal implementation ability, depending on dosage forms.

The method of administrating the pharmaceutical of the present invention is not particularly limited, but in the case of parenteral formulations, there can be exemplified, for example, intravascular administration (preferably intravenous administration), intraperitoneal administration, intestinal administration, and subcutaneous administration. In one preferred embodiment, the pharmaceutical of the present invention is administered to a living body by intravenous administration. In addition, the pharmaceutical of the present invention may be used in combination with other pharmaceuticals, depending on the disease to be prevented and/or treated.

A third aspect of the present invention relates to a method for preventing and/or treating diseases in which Th2-type cytokines are effective, comprising administering a pharmaceutical containing an effective amount of dendritic cells pulsed with α-GalCer to a subject. The meaning of each term in the third aspect is the same as described in the first aspect mentioned above.

The present invention will be described in more detail by the following examples. However, these examples are intended to aid the understanding of the present invention, and the technical scope of the present invention is not limited thereto.

EXAMPLES

Example 1 Preparation of Dendritic Cells Pulsed with α-GalCer

Dendritic cells pulsed with α-GalCer were prepared according to the method described in Non-Patent Literature 11. The following shows a concrete procedure.

(1) Preparation of Mononuclear Cells

Cell fraction was collected from healthy adult donor blood by apheresis using a continuous blood component separation device.

The cell fraction (26.6 mL) was layered onto 20 mL of Ficoll-Paque PREMIUM (GE Healthcare Japan) in a 50 mL centrifuge tube, and centrifuged for 30 minutes at 400×g and 20° C. to collect a mononuclear cell layer. The mononuclear cell layer was washed with the same amount of saline, and centrifuged for 10 minutes at 400×g and 20° C. AIM-V medium supplemented with albuminate (prepared by adding 1 part by volume of 4.4% donated blood albuminate (Nippon Pharmaceutical Co., Ltd.) to 20 parts by volume of AIM-V medium (GIBCO Invitrogen Corporation)) was added to the precipitate to make a suspension volume of 45 mL, and the suspension was centrifuged again. After this operation was repeated one more time, the resulting precipitate was suspended in AIM-V medium supplemented with autologous plasma and alubminate (prepared by adding 1 part by volume of healthy adult donor plasma and 2 parts by volume of 4.4% donated blood alubminate to 40 parts by volume of AIM-V medium), and the suspension was adjusted to a cell concentration of $2.7 \times 10^8$ cells/mL or less to obtain a cell suspension.

The cell suspension (13.8 mL) was dispensed into a 25 mL frozen bag, and 2 mL of anti-coagulant solution, ACD-A solution (Terumo Corporation) and 9.2 mL of frost protection solution CP-1 (Kyokuto Pharmaceutical Industrial Co., Ltd.) were added to each bag. Then, the bags were cryopreserved at −80° C.

(2) Preparation of Dendritic Cells Pulsed with α-GalCer

The mononuclear cells cryopreserved in (1) were thawed at 37° C., and washed by adding 2 parts by volume of 4.4% donated blood albuminate followed by centrifugation at 400×g and 20° C. for 5 minutes. The precipitate was washed again by adding saline (45 mL) supplemented with albuminate followed by centrifugation to obtain mononuclear cells as the precipitate.

The mononuclear cells ($1 \times 10^8$ cells) were seeded into a 225 cm$^2$ flask, and cultured at 37° C. under 5.0% $CO_2$ for 7 days, using 50 mL of AIM-V medium supplemented with autologous plasma and alubuminate to which were added human IL-2 (Shionogi & Co., Ltd.) at a final concentration of 100 JRU/mL and human GM-CSF (North China Pharmaceutical Group Corporation-GeneTech) at a final concentration of 800 U/mL. On days 3 and 6 of the culture, 50 mL of AIM-V medium supplemented with autologous plasma and alubuminate was further added, and human IL-2 and human GM-CSF were added to final concentration of 100 JRU/mL and 800 U/mL, respectively. On day 6 of the culture, α-GalCer (Funakoshi Co., Ltd.) was added thereto to a final concentration of 100 ng/mL.

After completion of the culture, the cells were collected from the flask with a cell scraper and by pipetting, filtered through a cell strainer, washed with 4.5 mL of saline supplemented with albumin (obtained by adding 1 part by volume of 25% donated blood albumin (The Chemo-Sero-Therapeutic Research Institute) to 10 parts by volume of saline), and centrifuged at 400×g and 20° C. for 5 minutes. The precipitate was washed three more times in the same manner as above and suspended in 10 mL of saline supplemented with albumin. The total amount of the cell suspension was collected with a syringe and added into a 50 mL saline bottle. This was used in the following examples as dendritic cells with α-GalCer (α-GalCer/DC)

Further, dendritic cells without α-GalCer (DC) were prepared in the same manner as above, except that α-GalCer was not added, and were used in the following examples.

Example 2 Therapeutic Effect on Post-Myocardial Infarction Heart Failure Model Mouse A test using myocardial infarction model mice was performed in order to evaluate the therapeutic effect of α-GalCer/DC on myocardial infarction. The myocardial infarction model mice were produced in accordance with the method described in Non-Patent Literature 8. That is, 10 to 12-week-old male C57BL/6J mice were anesthetized by the administration of pentobarbital (50 mg/kg body weight), and a throracotomy of the left side chest was performed and the left anterior descending coronary artery was ligated with an 8-0 thread, thereby to cause myocardial infarction.

Mice after myocardial infarction were divided into two groups, i.e. α-GalCer/DC group (n=32) and PBS group (n=38). On days 1 and 4 after the surgery, $3 \times 10^6$ cells of α-GalCer/DC of example 1 suspended in 200 μL of PBS was intravenously administered to the α-GalCer/DC group, and 200 μL of PBS was intravenously administered to the PBS group. The mice were kept for 4 weeks after the surgery and then a survival curve was generated by the Kaplan-Meier method.

Echocardiography was performed to evaluate the cardiac function 4 weeks after the surgery. The echocardiography was carried out by using an ultrasound recording device EUB-8000 (Hitachi, Ltd.) under anesthesia with pentobarbital. The left ventricular end-diastolic diameter and left ventricular end-systolic diameter were measured from the echo image, and the left ventricular fractional shortening, which is an index of the left ventricular contractility, was calculated as (left ventricular end-diastolic diameter−left ventricular end-systolic diameter)/left ventricular end-diastolic diameter×100.

Figure 1:
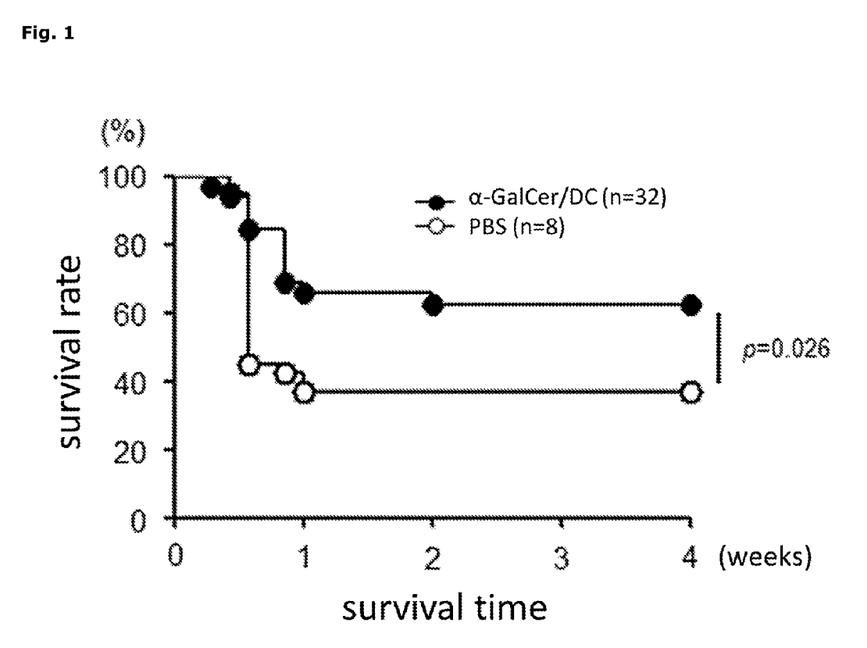
FIG. 1 is a graph showing the survival rate of post-myocardial infarction heart failure model mice administered with PBS or α-GalCer/DC.
Figure 2:
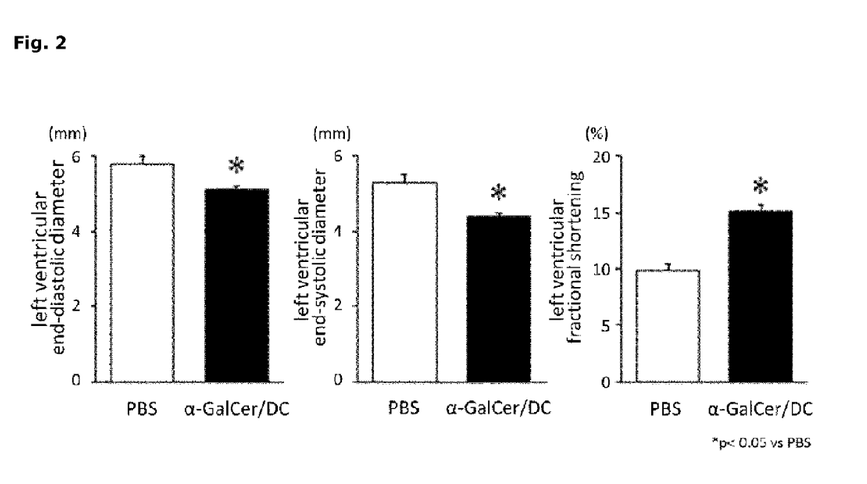
FIG. 2 is graphs showing left ventricular end-diastolic diameter (left), left ventricular end-systolic diameter (center), and left ventricular fractional shortening (right) in post myocardial infarction heart failure model mice administered with PBS or α-GalCer/DC.

The results are shown in FIGS. 1 and 2. In the PBS group, more than half of the individuals died due to heart failure and myocardial rupture in the infarct site within one week after the surgery. However, in the α-GalCer/DC administration group, myocardial rupture in the acute phase was decreased, and the survival rate at the end of observation period was also significantly improved (FIG. 1).

The left ventricular end-diastolic diameter is about 6 mm in the PBS group, exhibiting the left ventricular enlargement due to left ventricular remodeling after the onset of myocardial infarction. On the other hand, the left ventricular end-diastolic diameter of the α-GalCer/DC administration group was significantly smaller than that of the PBS group, suggesting that the progression of left ventricular remodeling after the onset of myocardial infarction was suppressed by the administration of α-GalCer/DC (FIG. 2, left). In the α-GalCer/DC administration group, the left ventricular end-systolic diameter was significantly smaller compared to the PBS group (FIG. 2, center). Further, the left ventricular fractional shortening (%) of the PBS group was about 10%, showing a significant decrease due to the onset of myocardial infarction, while that of the α-GalCer/DC administration group was about 15%, which was significantly greater compared to the PBS group (FIG. 2, right).

From the above results, it was confirmed that post-myocardial infarction heart failure and cardiac function in mice have been improved with the human α-GalCer/DC of example 1.

Example 3 Therapeutic Effect on Myocardial Ischemia-Reperfusion Model Mouse

In order to evaluate the therapeutic effect of α-GalCer/DC on ischemia-reperfusion, a test using myocardial ischemia-reperfusion model mice was performed. The mouse α-GalCer/DC and the mouse DC without α-GalCer, used in the test, were prepared by the same procedure as in example 1, using mononuclear cells isolated from mouse peripheral blood.

Myocardial ischemia-reperfusion model mice were produced according to the method described in Non-Patent Literature 9. That is, 10 to 12 week-old male C57BL/6J mice were divided into three groups of α-GalCer/DC group (n=10), DC group (n=7) and PBS group (n=8), and all mice were subjected to ischemia-reperfusion surgery in accordance with the following procedure. Under anesthesia with pentobarbital (50 mg/kg body weight), a throracotomy of the left side chest was performed to ligate the left anterior descending coronary artery three times with an 8-0 thread, together with a polyethlen-10 tube placed on the coronary artery. The occurrence of the ischemia was confirmed by observing the color change in the cardiac muscle to white.

15 minutes after the onset of ischemia, mouse α-GalCer/DC ($3 \times 10^6$ cells) suspended in 200 μL of PBS was intravenously administered to the α-GalCer/DC group; mouse DC without α-GalCer ($3 \times 10^6$ cells) suspended in 200 μL of PBS was intravenously administered to the DC group; and 200 μL of PBS was intravenously administered to the PBS group. After 45 minutes of ischemia time, the thread used to ligate the coronary artery was cut and the polyethlen-10 tube was removed for reperfusion. The reperfusion was confirmed by observing the color change in the cardiac muscle from white to red.

Subsequently, the extent of myocardial ischemia and infarction was evaluated by staining with Evans Blue and TTC as follows.

24 hours after the reperfusion, mice were subjected to laparotomy under anesthesia with 2,2,2-tribromoethanol (2.5% wt/vol, 8 μL/g body weight) to expose the inferior vena cava. The left chest was subjected again to thoracotomy and the coronary artery was re-ligated with an 8-0 thread at the same position as the site ligated in the ischemia-reperfusion surgery. After the ligation, a syringe with a three-way stopcock was promptly punctured to the inferior vena cava to collect blood. Changing the direction of the three-way stopcock while the syringe being stabbed, 0.5 mL of 4% Evans Blue (Wako) was intravenously administered through the inferior vena cava to stain a non-ischemic region with Evans Blue, thereby to distinguish an ischemic region and a non-ischemic region.

After administration of Evans Blue, the heart was immediately removed, washed with PBS at 4° C., and both atriums and the right ventricle were excised to isolate only the left ventricle. After the isolated left ventricle was immersed in liquid nitrogen for 15 seconds, the left ventricle was cut annularly with a razor under a microscope so that the ventricular apex was divided into 5 equal parts in the long axis direction from the ligation site. Four slices of the left ventricle except for the ventricular apex end were immersed in 1.5% 2,3,5-triphenyltetrazolium chloride (TTC, Wako), reacted at 37° C. for 15 minutes to stain the non-infarcted region in red, and fixed by immersing in 10% formalin solution at room temperature for 15 minutes. The apical side of each of the left ventricle slices was imaged under a microscope and measured the weight. An example of the imaged left ventricle slices is shown in the upper photographs of FIG. 3. The areas of white region, red region, and blue region of the left ventricular slice image were measured respectively using Image J (National Institutes of Health, Bethesda, Md.), and the percentage of each area to the whole was calculated. Then, the weight of each area was approximately calculated by multiplying the area percentage by the weight for each of the left ventricular slices, thereby to calculate the sum weight of 4 slices in each area.

By a series of staining, the "infarct area" of the cardiac muscle exhibits white, the "non-infarct ischemia area" (area where no infarction occurred, but ischemic injury occurred) exhibits red, and the "non-ischemic area" exhibits blue. The total weight of the white area was calculated as an infarct size (IS); the total weight of the white area and the red area was calculated as an area exposed to ischemia (area at risk: AAR); and the total weight of the white area, the red area, and the blue area was calculated as an entire left ventricle weight (left ventricle: LV). Then, the extent of ischemia and infarction of the left ventricular myocardium was evaluated, using the proportion of the area at risk to the entire left ventricle (AAR/LV) and the proportion of the area having led to the infarction to the area at risk (IS/AAR) respectively as an index.

Figure 3:
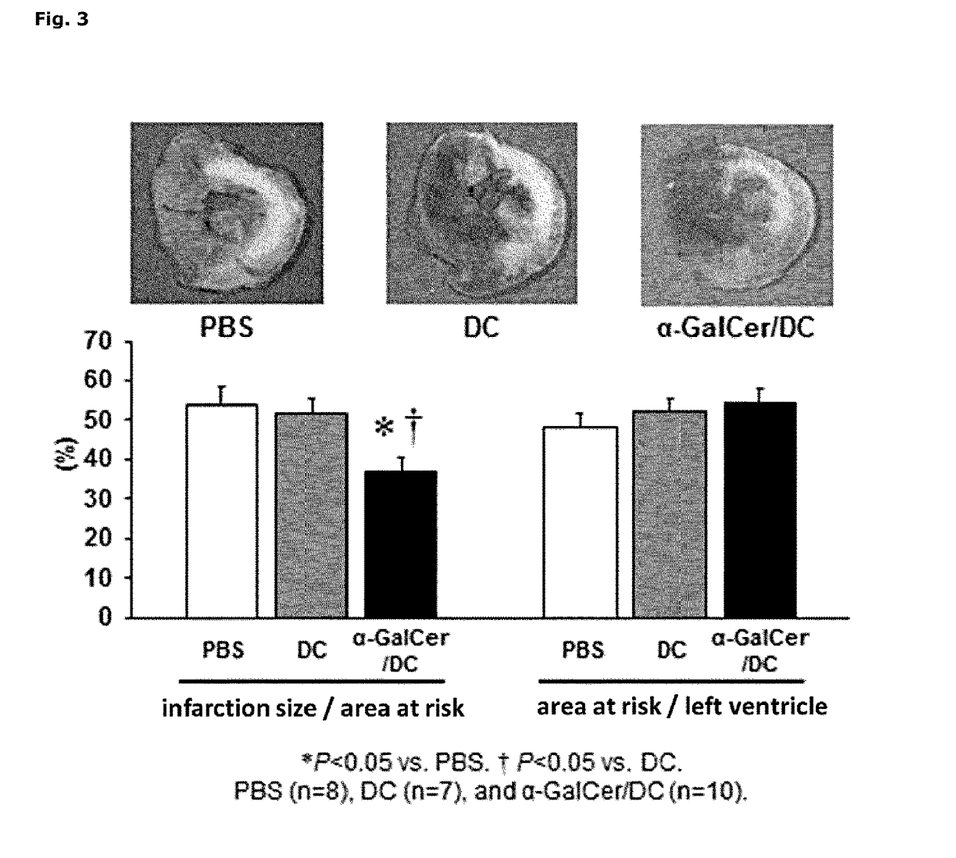
FIG. 3 is figures showing a state of myocardial infarction and ischemia in myocardial ischemia-reperfusion model mice administered with PBS, DC, or α-GalCer/DC. The upper section is photographs showing an example of left ventricle slices of the heart stained with Evans Blue and TTC, and the lower section is a graph of infarct size (left) and ischemia risk range (right) calculated on the basis of the staining results.

The results are shown in FIG. 3. The extent of the infarct (FIG. 3, bottom left) in the DC group was comparable to that of the PBS group, while the extent of the infarct was decreased significantly in the α-GalCer/DC group, revealing that α-GalCer/DC reduced ischemia-reperfusion injury. There was no significant difference among the three groups with respect to the extent of ischemia (FIG. 3, lower right).

Where it is very important to control the immune response of NKT cells in cell immunotherapy using NKT cells, it was rather believed that the use of α-GalCer/DC for the treatment of cardiovascular diseases, produced by the method described in Non-Patent Literature 11 and known to shift the NKT cells toward Th1 type, would lead to disease exacerbation. However, it was demonstrated by the Examples that α-GalCer/DC produced in the same manner as in Non-Patent Literature 11, contrary to conventional expectations, exhibited therapeutic effects on post-myocardial infarction heart failure and ischemia-reperfusion injury.

INDUSTRIAL APPLICABILITY

According to the present invention, by using dendritic cells prepared by the method proven in cellular immunotherapy, it becomes possible to prevent and/or treat diseases in which Th2-type cytokines are effective. Since the method for preparing dendritic cells has been proven to be successful in cellular immunotherapy of cancer, said method is reliable and its clinical application is relatively easy compared to other cellular immunotherapy.

The invention claimed is:
1. A method for treating myocardial infarction or its complications, ischemia-reperfusion injury, or aneurysm, comprising administering a pharmaceutical containing an effective amount of dendritic cells pulsed with α-galactosylceramide to a subject, wherein the dendritic cells are obtained by a method comprising the steps of:
   culturing mononuclear cells in the presence of GM-CSF and IL-2,
   pulsing the cultured cells with α-galactosylceramide, and
   obtaining dendritic cells pulsed with α-galactosylceramide.

* * * * *